(12) United States Patent
Dabbah

(10) Patent No.: US 10,729,474 B2
(45) Date of Patent: Aug. 4, 2020

(54) BONE PLATES, SYSTEMS, AND METHODS OF USE

(71) Applicant: K2M, Inc., Leesburg, VA (US)

(72) Inventor: Michael Dabbah, Owings Mills, MD (US)

(73) Assignee: K2M, Inc., Leesburg, VA (US)

(*) Notice: Subject to any disclaimer, the term of this patent is extended or adjusted under 35 U.S.C. 154(b) by 210 days.

(21) Appl. No.: 15/704,052

(22) Filed: Sep. 14, 2017

(65) Prior Publication Data
US 2018/0070992 A1 Mar. 15, 2018

Related U.S. Application Data

(60) Provisional application No. 62/394,422, filed on Sep. 14, 2016.

(51) Int. Cl.
*A61B 17/70* (2006.01)
*A61B 17/80* (2006.01)

(52) U.S. Cl.
CPC ...... *A61B 17/7059* (2013.01); *A61B 17/8004* (2013.01); *A61B 17/8052* (2013.01); *A61B 17/8057* (2013.01); *A61B 17/8085* (2013.01)

(58) Field of Classification Search
CPC . A61B 17/7059; A61B 17/80; A61B 17/7077; A61B 17/8052; A61B 17/8004
See application file for complete search history.

(56) References Cited

U.S. PATENT DOCUMENTS

| | | | |
|---|---|---|---|
| 4,929,247 A * | 5/1990 | Rayhack | A61B 17/8019 606/105 |
| 5,360,452 A | 11/1994 | Engelhardt et al. | |
| 5,403,136 A | 4/1995 | Mathys | |
| 5,593,410 A | 1/1997 | Vrespa | |
| 5,601,553 A | 2/1997 | Trebing et al. | |
| 5,681,311 A * | 10/1997 | Foley | A61B 17/7059 606/283 |
| 5,797,914 A | 8/1998 | Leibinger | |
| 6,030,162 A | 2/2000 | Huebner | |
| 6,129,730 A | 10/2000 | Bono et al. | |
| 6,152,927 A | 11/2000 | Farris et al. | |
| 6,322,562 B1 | 11/2001 | Wolter | |
| 6,328,738 B1 | 12/2001 | Suddaby | |
| 6,344,042 B1 | 2/2002 | Curtis et al. | |
| 6,398,783 B1 | 6/2002 | Michelson | |
| 6,428,542 B1 | 8/2002 | Michelson | |
| 6,547,564 B1 | 4/2003 | Hansson | |
| 6,592,586 B1 | 7/2003 | Michelson | |
| 6,616,669 B2 | 9/2003 | Ogilvie et al. | |
| 6,669,700 B1 | 12/2003 | Farris et al. | |
| 6,916,320 B2 | 7/2005 | Michelson | |
| 6,926,718 B1 | 8/2005 | Michelson | |

(Continued)

Primary Examiner — Andrew Yang
(74) Attorney, Agent, or Firm — Lerner, David, Littenberg, Krumholz & Mentlik, LLP

(57) ABSTRACT

A bone plate is provided including a top and bottom surface. The bottom surface may be adapted to contact bone. The bone plate may further include a plurality of apertures, wherein each aperture includes an annular sidewall and a lip adjacent to the bottom surface of the bone plate. The bone plate may also include at least one slot, wherein the slot includes a sidewall and a lip adjacent to the bottom surface of the bone plate. A bone plate system and method of use are also provided.

20 Claims, 12 Drawing Sheets

(56) References Cited

U.S. PATENT DOCUMENTS

| | | |
|---|---|---|
| 6,936,050 B2 | 8/2005 | Michelson |
| 6,936,051 B2 | 8/2005 | Michelson |
| 6,955,677 B2 | 10/2005 | Dahners |
| 7,001,387 B2 | 2/2006 | Farris et al. |
| 7,074,221 B2 | 7/2006 | Michelson |
| 2002/0188296 A1* | 12/2002 | Michelson ......... A61B 17/7059 606/71 |

* cited by examiner

BONE PLATES, SYSTEMS, AND METHODS OF USE

CROSS-REFERENCE TO RELATED APPLICATIONS

The present application claims the benefit of and priority to U.S. Provisional Application Ser. No. 62/394,422 filed on Sep. 14, 2016, the entire contents of which is incorporated by reference herein.

BACKGROUND

Technical Field

The present disclosure relates generally to devices and methods for treating spinal conditions, and in particular, to bone plates, systems, and methods for fixation and stabilization of the spine.

Background of the Disclosure

The human spinal column is a highly complex structure. It includes twenty-four discrete bones, known as vertebrae, coupled sequentially to one another to house and protect critical elements of the nervous system. In between adjacent vertebrae is a disc. Each disc functions as a shock absorber, absorbing the impact of the body's activities and distributing pressure under compressive loads. Additionally, each disc forms a fibro-cartilaginous joint between adjacent vertebrae, allowing movement of the vertebrae and acting as a ligament to hold the vertebrae together.

For many reasons, such as aging and trauma, the discs may begin to deteriorate and weaken, potentially resulting in chronic pain, degenerative disc disease, or even tearing of the disc. Ultimately, the disc may deteriorate or weaken to the point of herniation, in which the inner portions of the disc protrude through the tear. A herniated disc may press against, or pinch, the spinal nerves, thereby causing radiating pain, numbness, tingling, and/or diminished strength or range of motion. The surgical removal of a diseased disc is a common procedure in current medical practice. Spinal fusion procedures involve removing a damaged disc and replacing it with an artificial disc, such as a bone graft or bone graft substitute. To keep the artificial disc and the vertebrae fixed in place while bone healing occurs, an external fixation device, such as a bone plate, is used. Bone plates are secured to the vertebrae using bone screws, which typically require drilling holes into the vertebrae.

The size of vertebrae and the spacing between vertebrae varies from patient to patient. The height of the vertebrae and the discs between them may vary level by level even in the same person. This typically becomes a problem when working across at least three vertebrae, i.e., when using two level bone plates. In order to cover the possible range of sizes, health care facilities must carry a large inventory of different sized plates. Another problem is that the holes made into the vertebrae act as a stress concentration within the vertebrae (as would any empty opening or crack within a rigid structural member) and predisposes the vertebrae to bone fracture, screw/plate migration, and/or vertebral failure.

Thus, there exists a need for an apparatus and/or method for performing spinal fusion with increased plate placement flexibility without unnecessarily compromising the structural rigidity of the vertebrae.

SUMMARY

In accordance with aspects of the present disclosure, a bone plate is provided. The bone plate has a top surface and a bottom surface adapted to contact bone. The bone plate defines a plurality of apertures, wherein each aperture of the plurality of apertures includes an annular sidewall and a lip adjacent to the bottom surface of the bone plate. The lip extends inwardly from the annular sidewall and defines a planar surface extending from the annular sidewall towards a center of each aperture of the plurality of apertures. The bone plate also defines at least one slot, wherein the at least one slot includes a sidewall and a lip adjacent to the bottom surface of the bone plate. The lip of the at least one slot extends inwardly from the sidewall of the at least one slot and has a planar surface extending from the sidewall of the at least one slot towards a center of the at least one slot.

In another aspect of the present disclosure, the sidewall and lip of each aperture of the plurality of apertures are non-threaded.

In yet another aspect of the present disclosure, the sidewall and lip of the at least one slot are non-threaded.

In still another aspect of the present disclosure, the lip of each aperture of the plurality of apertures is configured to engage a bone screw such that the bone screw is retained therein.

In still yet another aspect of the present disclosure, the lip of the at least one slot is configured to engage a bone screw such that the bone screw is retained therein.

In another aspect of the present disclosure, the bone plate further includes at least one guide aperture positioned along a central longitudinal axis of the bone plate.

In yet another aspect of the present disclosure, the bone plate has a lordotic curvature.

In still another aspect of the present disclosure, the at least one slot is positioned along a central longitudinal axis of the bone plate.

In still yet another aspect of the present disclosure, the bone plate is formed from a material selected from a group consisting of stainless steel, polymer, titanium, titanium alloy, and ceramic.

In another aspect of the present disclosure, the bone plate is adapted to engage at least three vertebrae along the anterior cervical spine.

In accordance with another aspect of the present disclosure, a bone plate system is disclosed. The bone plate system includes a bone plate having a top surface and a bottom surface adapted to contact vertebrae. The bone plate defines a plurality of apertures, wherein each aperture of the plurality of apertures includes an annular sidewall and a lip adjacent to the bottom surface of the bone plate. The lip extends inwardly from the annular sidewall and defines a planar surface extending from the annular sidewall towards a center of the aperture of the plurality of apertures. The bone plate further defines at least one slot, wherein the at least one slot includes a sidewall and a lip adjacent to the bottom surface of the bone plate. The lip of the at least one slot extends inwardly from the sidewall of the at least one slot and defines a planar surface extending from the sidewall of the at least one slot towards a center of the at least one slot. First and second distraction screws attachable to respective first and second vertebrae are included in the system as well as a distraction instrument attachable to the first and second distraction screws. The distraction instrument is adapted to distract the first and second vertebrae.

In another aspect of the present system, a plurality of bone screws are configured to be driven into vertebrae.

In yet another aspect of the present system, each bone screw of the plurality of bone screws includes a shank having a first helical thread disposed thereon and a second helical thread disposed on a head portion thereof. The first helical thread of the shank is adapted for insertion into a vertebra and the second helical thread is adapted for engagement with the lip of each aperture of the plurality of apertures or the lip of the at least one slot.

According to another aspect of the present disclosure is a method of performing a spinal procedure. The method includes inserting distraction screws into distraction screw holes formed in first and second vertebrae, distracting the first and second vertebrae using a distraction instrument coupled to the distraction screws, removing at least a portion of an intervertebral disc located between the first and second vertebrae, removing the distraction screws, and inserting a first bone screw through a slot of the bone plate into the distraction screw hole of the first vertebra.

In another aspect of the present disclosure, the method includes adjusting the slot over the distraction screw hole of the first vertebra, such that the bone plate can be shifted in the cephalad or caudal direction about the slot for proper alignment of the bone plate onto the second and a third vertebra.

In yet another aspect of the present disclosure, the method includes inserting a second bone screw through a first aperture of a bone plate into the second vertebra.

In still another aspect of the present disclosure, the method includes inserting a third bone screw through a second aperture of the bone plate into the third vertebra.

In still yet another aspect of the present disclosure, inserting the first bone screw includes the bone plate having a top surface and a bottom surface adapted to contact vertebrae, a plurality of apertures, wherein each aperture of the plurality of apertures includes an annular non-threaded sidewall and a non-threaded lip adjacent to the bottom surface of the bone plate, the lip extending inwardly from the sidewall and defining a planar surface extending from the sidewall towards a center of each aperture of the plurality of apertures, and a slot in the bone plate including a non-threaded sidewall and a non-threaded lip adjacent to the bottom surface of the bone plate. The lip extends inwardly from the sidewall and defines a planar surface extending from the sidewall towards a center of the slot.

In another aspect of the present disclosure, the method includes fastening the bone plate to at least three vertebrae along the anterior cervical spine.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Figure 1:
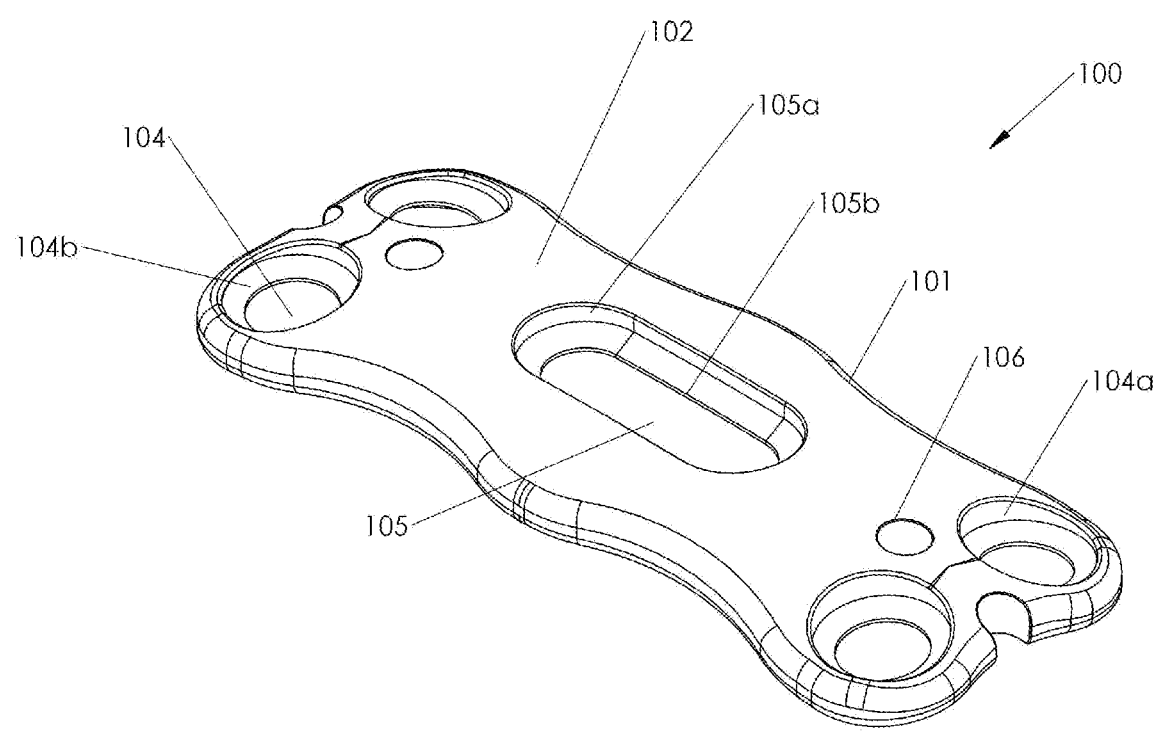
FIG. 1 is an isometric view of an embodiment of a vertebral plate in accordance with the present disclosure.
Figure 2:
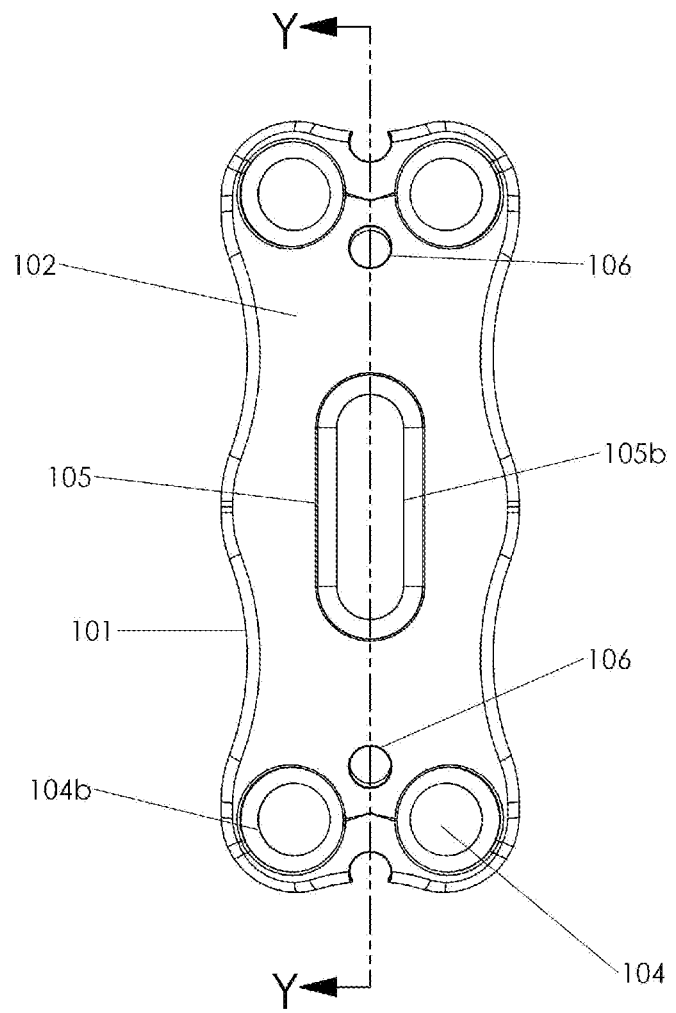
FIG. 2 is a top view of the vertebral plate of FIG. 1.
Figure 3:
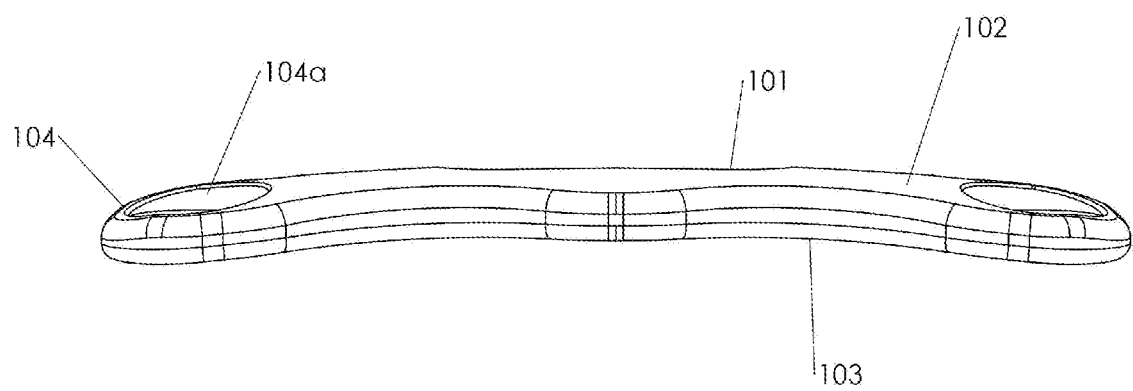
FIG. 3 is a side view of the vertebral plate of FIG. 1.
Figure 4:
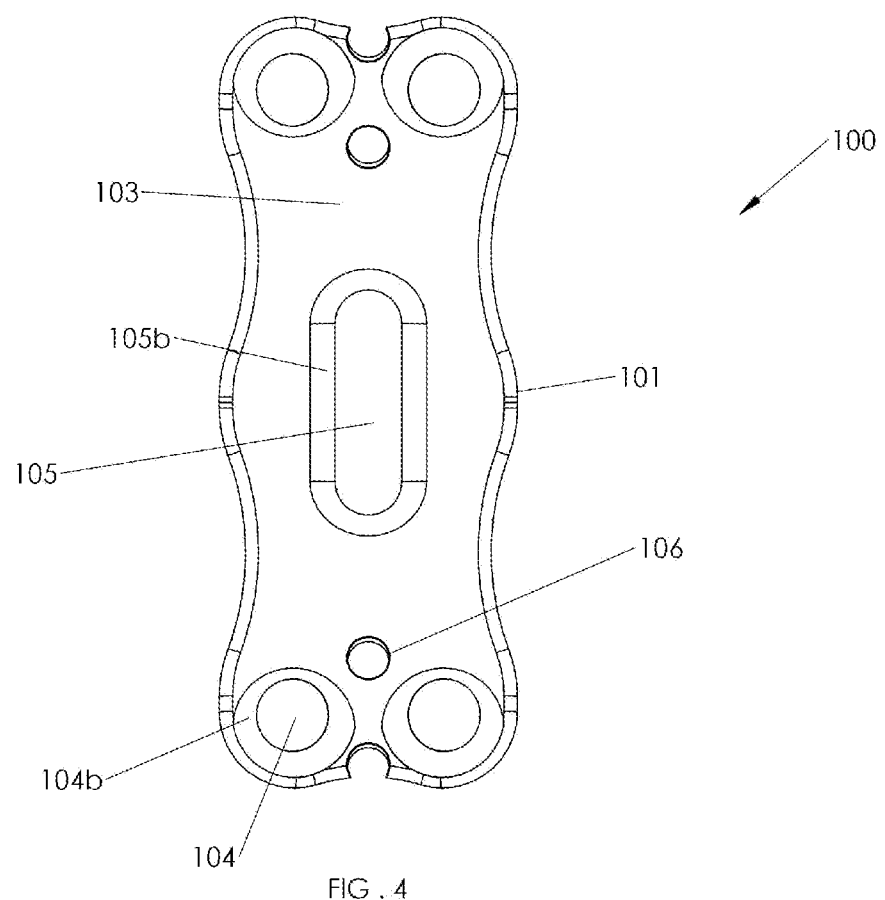
FIG. 4 is a bottom view of the vertebral plate of FIG. 1.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudal" indicates a direction toward the patient's feet. Further still, for the purposes of this application, the term "lateral" indicates a direction toward a side of the body of the patient, i.e., away from the middle of the body of the patient, and the term "medial" indicates a direction toward the inside of the body of the patient, i.e., toward the middle of the body of the patient. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

In accordance with the present disclosure, as illustrated in FIGS. 1-4, a bone plate or vertebral plate 100 is provided and generally includes a body 101, a top surface 102, a bottom surface 103, apertures 104, a slot 105, and guide openings 106. Vertebral plate 100 as shown may be a two level plate, i.e., designed for bridging three vertebrae.

Body 101 of vertebral plate 100 is generally shown as having a rectangular profile, but any suitable profile for placement over vertebrae may be used. Vertebral plate 100 is illustrated as having a lordotic curvature such that it is better suited to fit the natural curvature of the anatomy, and to minimize the amount of intraoperative contouring required. In embodiments, if additional curvature of vertebral plate 100 is required, a plate bender may be used to adjust the contour of the plate to better conform to the anatomy of the patient by adding additional lordosis, or kyphosis, to the plate. In embodiments, vertebral plate 100 may be constructed of stainless steel, polymer, titanium, titanium alloy, ceramic, or any other suitable biocompatible material having sufficient rigidity. In embodiments, vertebral plate 100 may be available in different configurations (e.g., size, type of metal used, etc.) and may be anodized into different colors (e.g., green, blue, purple, etc.) to indicate the specific configuration of vertebral plate 100 to the user.

Vertebral plate 100 includes a plurality of apertures 104 and one or more guide openings 106, wherein the apertures 104 and one or more guide openings 106 extend through the thickness of vertebral plate 100. The one or more guide openings 106 are positioned along the central longitudinal axis Y-Y (FIG. 2) of vertebral plate 100. Guide openings 106 may be used for temporary fixation pins 110 (FIG. 8) to temporarily affix vertebral plate 100 to the vertebrae while proper placement is being determined. In other embodiments, guide openings 106 may be used as docking holes for positioning and/or stabilizing of other surgical instruments for use during, for example, an anterior cervical discectomy and fusion (ACDF) procedure. Each aperture 104 has an annular sidewall 104a extending downwards from the top surface 102 of vertebral plate 100. A lip 104b is located in each aperture 104 in proximity to the bottom surface 103 of vertebral plate 100. The lip 104b is configured for engaging a bone screw 200 (FIGS. 5 and 6).

Figure 5:
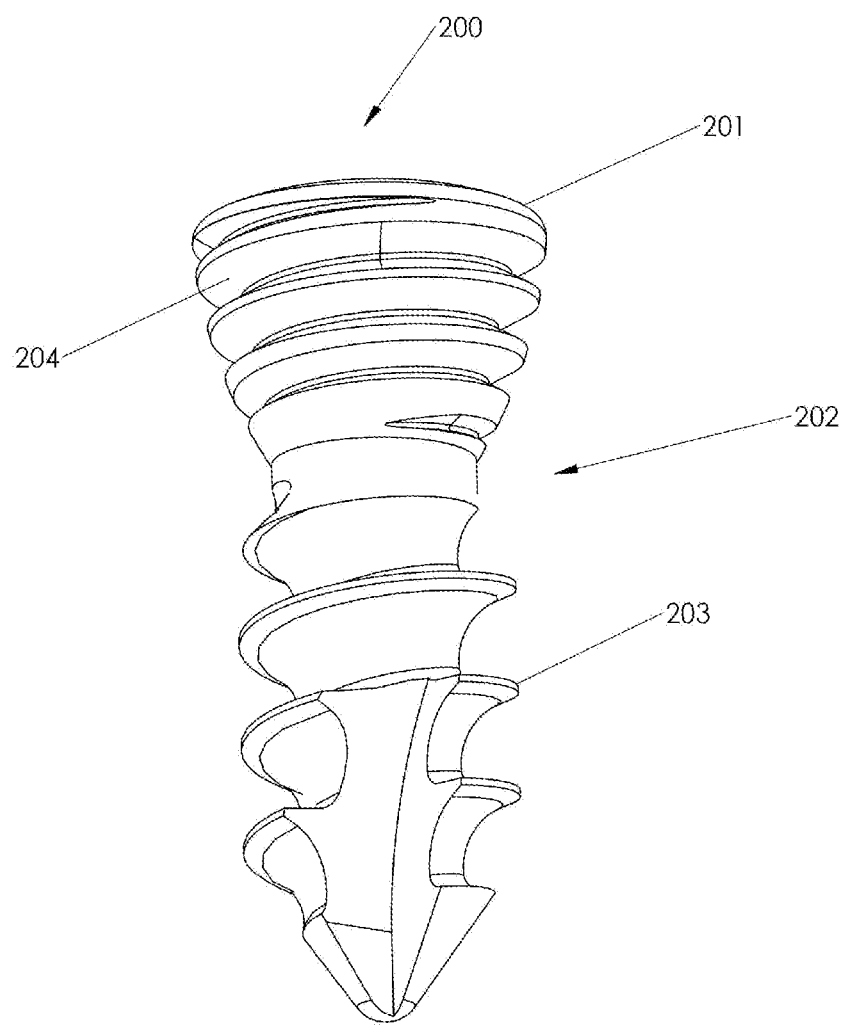
FIG. 5 is an isometric view of a bone screw usable with the bone plate of FIG. 1.
Figure 6:
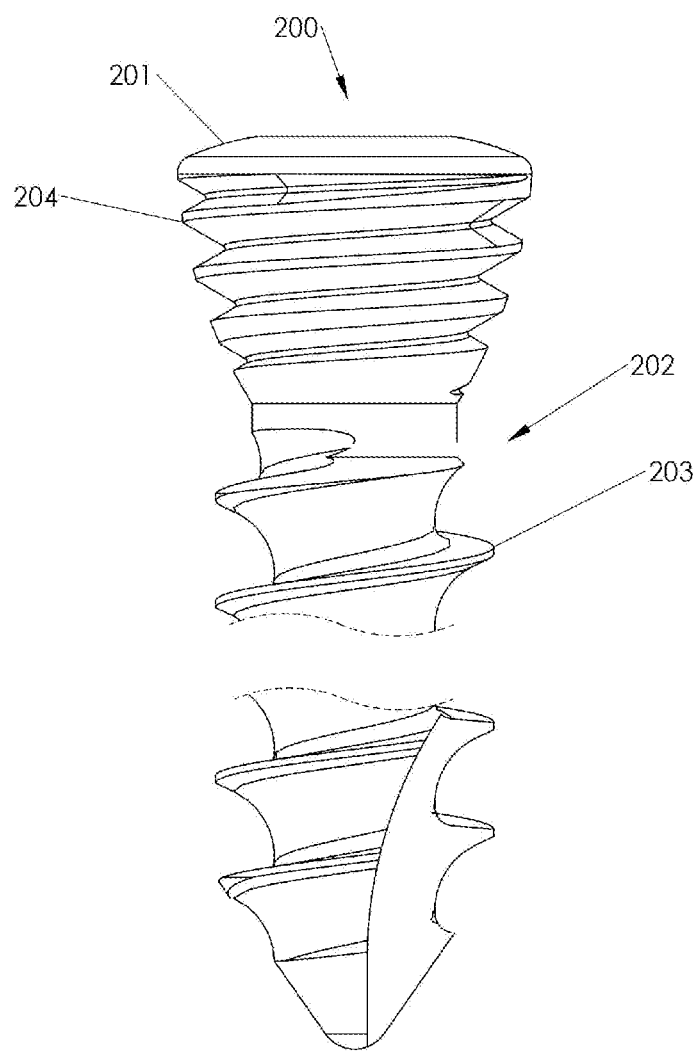
FIG. 6 is a side elevation view of the bone screw of FIG. 5.

Referring now to FIGS. 5 and 6, bone screw 200 may include an independent locking head 201 and a shank 202. The shank 202 may have a uniform outer diameter and a first helical thread 203 for threaded insertion into the vertebrae. Rotating bone screw 200 causes the threads of independent locking head 201 of the respective bone screw 200 to engage lip 104b. The independent locking head 201 includes a second helical thread 204 thereon such that each bone screw 200 is secured in the aperture 104 and resists backing out of the aperture 104. At the same time, a distal end of bone screw 200 remains pivotable, while a proximal end of bone screw 200 is constrained within the vertebral plate 100. It should be appreciated that aperture 104 may have any suitable size to accommodate any type of bone screw 200. In other embodiments, the pitch of first helical thread 203 may be greater than the pitch of second helical thread 204. In yet other embodiments, first helical thread 203 and second helical thread 204 may have a uniform pitch.

In embodiments, bone screw 200 may be 4.0 mm to 4.5 mm in diameter. In other embodiments, bone screw 200 is self-starting, self-tapping, or the like. In yet other embodiments, bone screws 200 may be positioned with up to 15 degrees of angulation in either direction, providing up to 30 degrees of conical angulation. If a greater angle is required for bone screws 200, a thread former may be used, providing up to 45 degrees of angulation. As mentioned, vertebral plate 100 may be bent anatomically without impairing the ability of the bone screws 200 to lock at any angle.

In embodiments, bone screws 200 are made of a titanium alloy that is preferably harder than the material used for vertebral plate 100. When inserted, bone screw 200 engages and reshapes lip 104b of aperture 104. Due to difference in material hardness and design, each independent locking head 201 of bone screw 200 begins to deform vertebral plate 100 through a reshaping process, which creates an autogenic lock to vertebral plate 100 upon insertion. It should be appreciated that the description of bone screws with vertebral plate 100 is merely illustrative and not meant to be limiting. For a detailed description of exemplary methods of using a vertebral plate with bone screws, reference may be made to U.S. Pat. No. 6,322,562, the entire contents of which is hereby incorporated by reference herein.

Although the following description describes one example of using vertebral plate 100, it is also envisioned that vertebral plate 100 may be used for any type of spinal fixation procedure.

Figure 7:
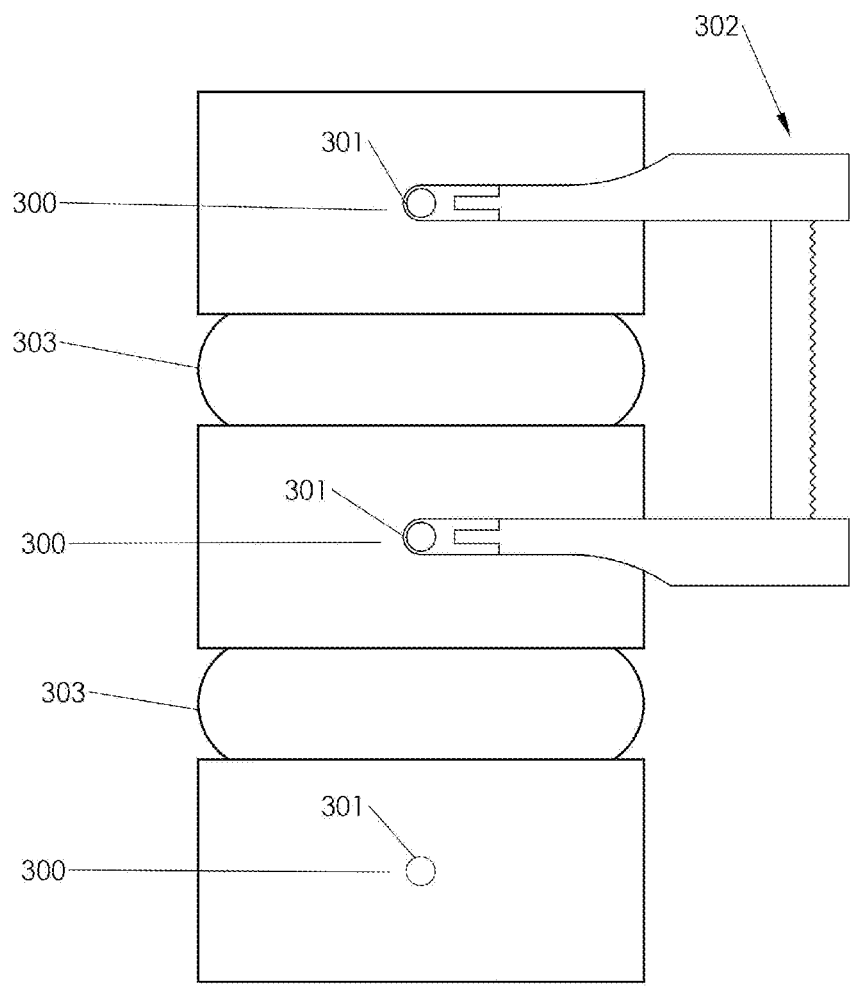
FIG. 7 is a top view of the vertebrae shown with a distraction instrument placed on distractor screws.

To prepare for ACDF, a surgeon will place the patient in a supine position, taking care to preserve sagittal alignment of the spine. An incision is made in the throat to expose the front of the cervical region of the spine. The surgeon will confirm whether the proper surgical level has been obtained, for example, the C4-C5-C6 vertebrae. Referring to FIG. 7, and after locating the discs to be removed, a temporary bone screw 301, commonly known as a distractor screw, or Caspar pin, is placed for threaded insertion into the center of each of the vertebra above and below the diseased disc space. A distraction pliers or instrument 302 is then placed over the temporary bone screws 301 and used to temporarily distract, or spread the vertebrae apart, such that the surgeon can work in the intervening disc space. The surgeon then removes the damaged disc(s) leaving an evacuated space between the vertebrae. Once the disc(s) are removed and the disc space(s) is exposed, a surgeon may then remove osteophytes from the anterior surfaces of the vertebrae, such that adequate surface contact can be made with bottom surface 103 of vertebral plate 100. To prevent the vertebrae from collapsing or rubbing together, an artificial disc(s) or bone graft 303 is inserted to fill the open disc space. The artificial disc serves as a bridge between the two vertebrae to create spinal fusion, so that over time, the two vertebrae are fused together to form one solid piece of bone.

Figure 8:
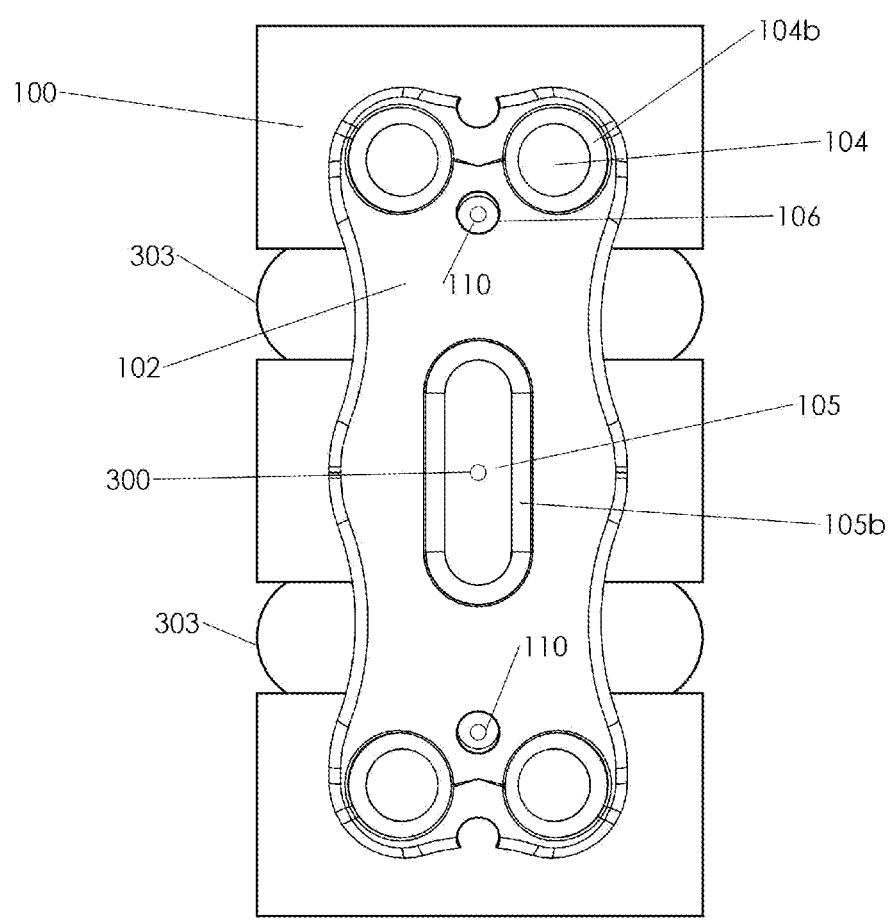
FIG. 8 is a top view of the vertebral plate of FIG. 1 positioned over the vertebrae of FIG. 7.

Referring now to FIG. 8, after the artificial disc 303 is in place, the temporary distraction screws are removed from the vertebrae, leaving behind distraction screw holes 300 in the center of each vertebra above and below the diseased disc space. Vertebral plate 100 is positioned over the C4-C5-C6 vertebrae. In an exemplary embodiment, slot 105 is positioned over the distractor screw hole 300 in an intermediate vertebra, such as, for example, C5, which is between C4 and C6. The size of vertebrae and the spacing between vertebrae varies from patient to patient. The height of the vertebrae and the discs between may vary level by level even in the same person. This typically becomes a problem when working across at least three vertebrae, i.e., when using at least two level plates. For example, if a surgeon is performing surgery across the C4-C5-C6 vertebrae, the C4-C5 level vertebrae may have a center-to-center distance 14 mm apart, while the C5-C6 level vertebrae may have a center-to-center distance 17 mm apart. Since standard vertebral plates are symmetric, a plate of correct length does not necessarily have bone screw receiving holes correctly positioned to overlie the vertebrae to which the plate is to be applied. For example, standard two level plates typically include three rows of screw holes with two screw holes on each row. Slot 105 provides the flexibility for allowing vertebral plate 100 to be secured to vertebrae about distractor hole 300 of the intermediate vertebrae to best fit vertebral plate 100 to the adjacent vertebrae. Slot 105 provides the surgeon the ability to move vertebral plate 100 in the cephalad or caudal direction about the slot 105 to achieve the desired fit over the vertebrae, instead of being forced to work within the confines of preset screw holes found in standard symmetric plates.

Advantageously, slot 105 also allows a surgeon to reuse distractor hole 300. For example, suitable bone screw(s) 200 may be inserted into distractor hole(s) 300 to secure vertebral plate 100 to the vertebrae. By reusing distractor hole 300 for bone screw 200, the surgeon need not drill two additional bone screw holes into the vertebra. The holes left by the distractor screw(s) may act as a stress concentration within the vertebrae, as would any empty opening or crack within a rigid structural member, and predisposes the vertebrae to bone fracture, screw/plate migration, and/or vertebral failure. Conventional bone plates typically require three holes made in each vertebra above and below the diseased disc space; two holes for securement of bone screws to the plate and one hole left by the removed distractor screw. The bone screw holes are made at separate and distinct locations from the distractor screw hole 300. The hole created by the distractor screw is typically necessary for successful ACDF surgery, since a distractor system is generally required to spread the vertebrae apart during the procedure.

In embodiments, slot 105 may have any suitable shape, such as, for example, oblong, oval, or ellipse. Slot 105 may include a sidewall 105a extending downwards from the top surface of vertebral plate 100. A slot lip 105b may be located in slot 105 in proximity to the bottom surface 103 of vertebral plate 100. The slot lip 105b is configured for engaging a bone screw 200. In embodiments, slot 105 may be disposed in the lateral direction. In embodiments, at least one aperture 104 may be replaced by at least one slot 105. In other embodiments, there may be a plurality of slots 105 replacing, for example, each row of apertures 104. In yet other embodiments, a unitary slot 105 may run from the top end of the vertebral plate 100 to the bottom end of vertebral plate 100. It should be appreciated that vertebral plate 100 may be designed with any combination of slots 105 and/or apertures 104, so long as the structural rigidity of vertebral plate 100 is maintained. In embodiments, distractor holes 300 may be reused at each vertebra, without the need to drill additional bone screw holes. In embodiments, distractor holes 300 may have a diameter smaller than the diameter of bone screws 200.

Figure 9:
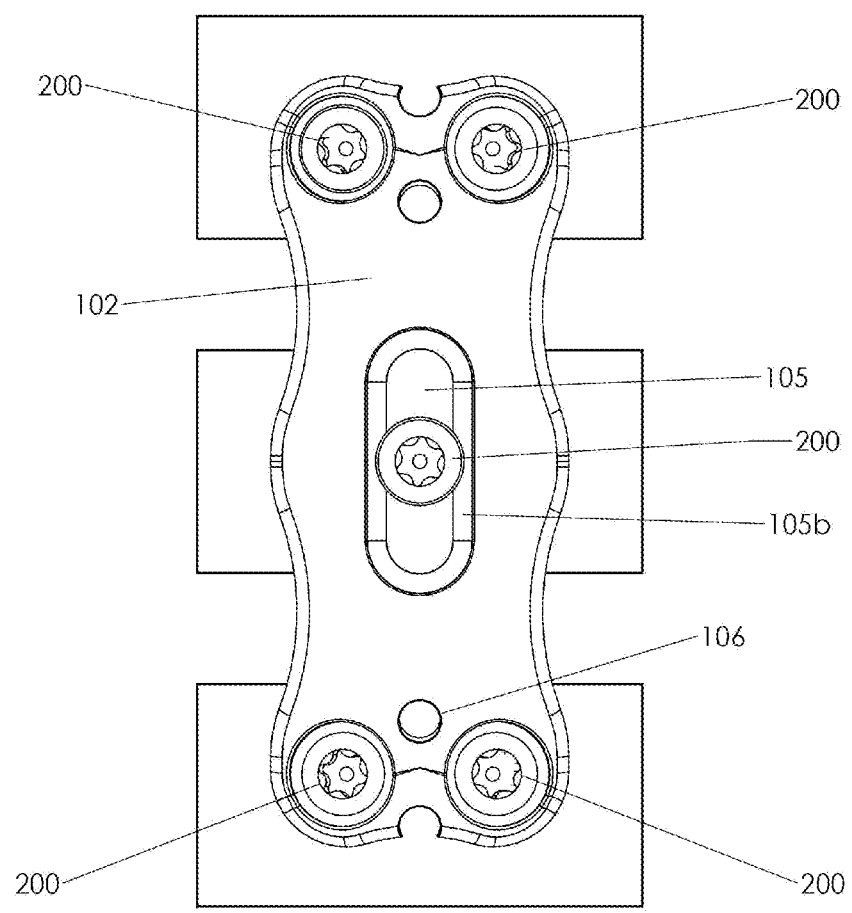
FIG. 9 is a top view of the vertebral plate of FIG. 1 affixed to the vertebrae of FIG. 8 with bone screws.
Figure 10:
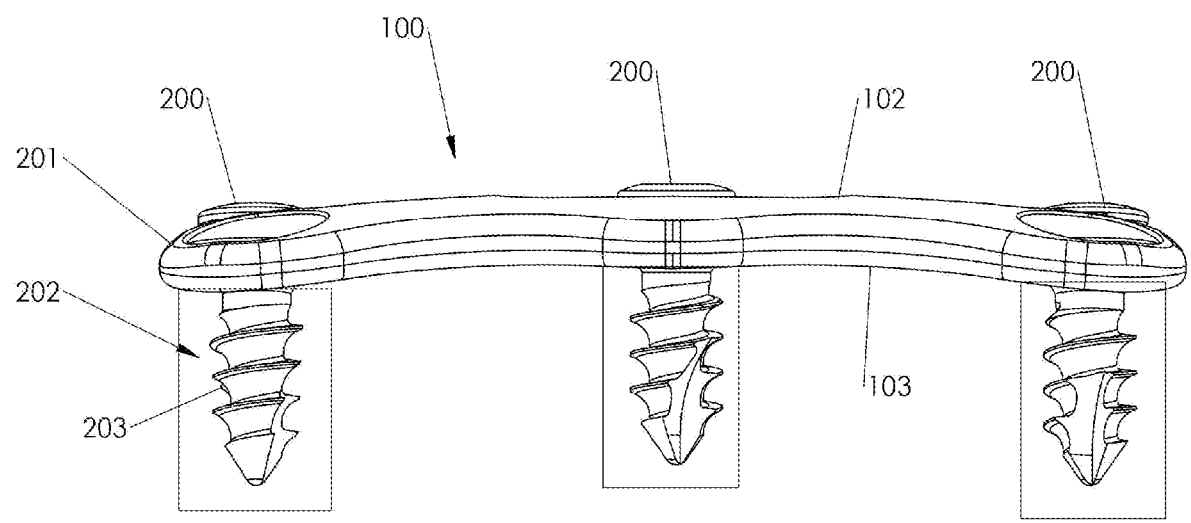
FIG. 10 is a side view of the vertebral plate of FIG. 1 affixed to the vertebrae of FIG. 9.

Referring now to FIG. 9 and FIG. 10, bone screws 200 are inserted through vertebral plate 100 and driven into the vertebrae for securement. In embodiments, a torque of 20 in-lbs applied to bone screw 200 is sufficient for proper affixment of vertebral plate 100 to the vertebrae. In embodiments, a bone reduction screw may be used to draw vertebral plate 100 closer to each vertebra before fastening vertebral plate 100 to the vertebrae.

Figure 11:
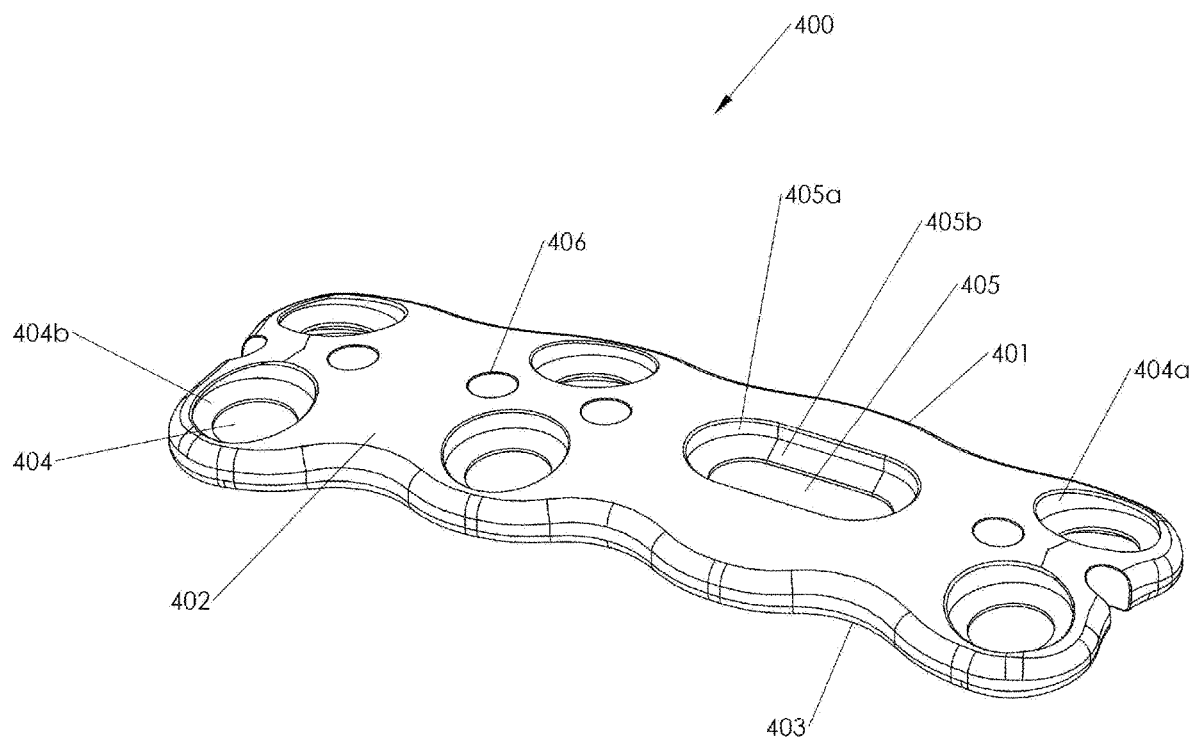
FIG. 11 is an isometric view of another embodiment of a vertebral plate according to the present disclosure.
Figure 12:
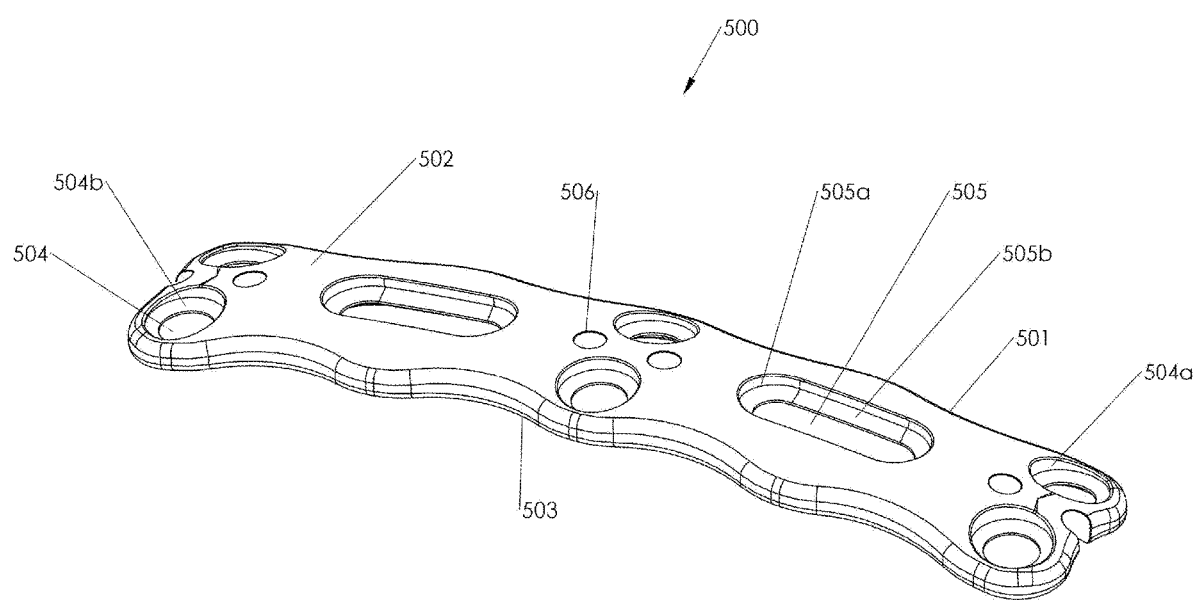
FIG. 12 is an isometric view of yet another embodiment of a vertebral plate according to the present disclosure.

Referring now to FIG. 11, another embodiment of a vertebral plate is shown, generally designated as 400. Vertebral plate 400 is a three level plate designed for bridging four vertebrae, for example, the C4-C5-C6-C7 vertebrae. Vertebral plate 400 generally includes a body 401, a top surface 402, a bottom surface 403, apertures 404 including sidewalls 404a and lips 404b, a slot 405, and guide openings 406. Referring now to FIG. 12, a four level vertebral plate is shown, generally designated as 500. Vertebral plate 500 likewise includes a body 501, a top surface 502, a bottom surface 503, apertures 504 including sidewalls 504a and lips 504b, a slot 505, and guide openings 506. Vertebral plate 500 may be used to bridge five vertebrae, such as, for example, the C3-C4-C5-C6-C7 vertebrae. Vertebral plates 400, 500 may generally include the features recited in the embodiments of vertebral plate 100.

It will be understood that various modifications may be made to the embodiments disclosed herein. Therefore, the above description should not be construed as limiting, but merely as exemplifications of embodiments. Those skilled in the art will envision other modifications within the scope and spirit of the claims appended hereto.

What is claimed is:

1. A bone plate, comprising:
a top surface and a bottom surface, the bottom surface adapted to contact bone;
a plurality of apertures defined in the bone plate and positioned at first and second ends thereof, wherein each aperture of the plurality of apertures includes an annular sidewall and a lip adjacent to the bottom surface of the bone plate, the lip extending inwardly from the annular sidewall and defining a planar surface extending from the annular sidewall towards a center of each aperture of the plurality of apertures; and
at least one slot defined in the bone plate between the first and second ends thereof, wherein the at least one slot defines an elongate opening at the top surface and an elongate opening at the bottom surface, the at least one slot includes a sidewall and a lip adjacent to the bottom surface of the bone plate, the lip of the at least one slot extending inwardly from the sidewall of the at least one slot and defining a planar surface extending from the sidewall of the at least one slot towards a center of the at least one slot.

2. The bone plate of claim 1, wherein the sidewall and the lip of each aperture of the plurality of apertures are non-threaded.

3. The bone plate of claim 1, wherein the sidewall and the lip of the at least one slot are non-threaded.

4. The bone plate of claim 1, wherein the lip of each aperture of the plurality of apertures is configured to engage a bone screw such that the bone screw is retained therein.

5. The bone plate of claim 1, wherein the lip of the at least one slot is configured to engage a bone screw such that the bone screw is retained therein.

6. The bone plate according to claim 1, wherein the bone plate further includes at least one guide aperture positioned along a central longitudinal axis of the bone plate.

7. The bone plate according to claim 1, wherein the bone plate has a lordotic curvature.

8. The bone plate according to claim 1, wherein the at least one slot is positioned along a central longitudinal axis of the bone plate.

9. The bone plate according to claim 1, wherein the bone plate is formed from a material selected from a group consisting of: stainless steel; polymer; titanium; titanium alloy; and ceramic.

10. The bone plate according to claim 1, wherein the bone plate is adapted to engage at least three vertebrae along the anterior cervical spine.

11. A bone plate system comprising:
a bone plate, including:
a top surface and a bottom surface, the bottom surface adapted to contact vertebrae;
a plurality of apertures defined in the bone plate, wherein each aperture of the plurality of apertures includes an annular sidewall and a lip adjacent to the bottom surface of the bone plate, the lip extending inwardly from the annular sidewall and defining a planar surface extending from the annular sidewall towards a center of the aperture of the plurality of apertures;
at least one slot defined in the bone plate, wherein the at least one slot includes a sidewall and a lip adjacent to the bottom surface of the bone plate, the lip of the at least one slot extending inwardly from the sidewall of the at least one slot and defining a planar surface extending from the sidewall of the at least one slot towards a center of the at least one slot;
first and second distraction screws attachable to respective first and second vertebrae; and
a distraction instrument attachable to the first and second distraction screws, the distraction instrument adapted to distract the first and second vertebrae.

12. The bone plate system of claim 11, further including a plurality of bone screws configured to be driven into vertebrae.

13. The bone plate system of claim 12, wherein each bone screw of the plurality of bone screws includes a shank having a first helical thread disposed thereon and a second helical thread disposed on a head portion thereof, the first helical thread of the shank is adapted for insertion into a vertebra and the second helical thread is adapted for engagement with the lip of each aperture of the plurality of apertures or the lip of the at least one slot.

14. A method of performing a spinal procedure, comprising:
inserting distraction screws into distraction screw holes formed in first and second vertebrae;
distracting the first and second vertebrae using a distraction instrument coupled to the distraction screws;
removing at least a portion of an intervertebral disc located between the first and second vertebrae;
removing the distraction screws; and
inserting a first bone screw through a slot of a bone plate into the distraction screw hole of the first vertebra.

15. The method according to claim 14, further comprising:
adjusting the slot over the distraction screw hole of the first vertebra, such that the bone plate can be shifted in the cephalad or caudal direction about the slot for proper alignment of the bone plate onto the second and a third vertebra.

16. The method according to claim 15, further comprising inserting a second bone screw through a first aperture of a bone plate into the second vertebra.

17. The method according to claim 16, further comprising inserting a third bone screw through a second aperture of the bone plate into the third vertebra.

18. The method according to claim 14, wherein inserting the first bone screw includes the bone plate having:
a top surface and a bottom surface, the bottom surface adapted to contact vertebrae; and
a plurality of apertures defined in the bone plate, wherein each aperture of the plurality of apertures includes an annular non-threaded sidewall and a non-threaded lip adjacent to the bottom surface of the bone plate, the lip extending inwardly from the sidewall and defining a planar surface extending from the sidewall towards a center of each aperture of the plurality of apertures, the slot defined in the bone plate includes a non-threaded sidewall and a non-threaded lip adjacent to the bottom surface of the bone plate, the lip of the slot extending inwardly from the sidewall of the slot and defining a planar surface extending from the sidewall of the slot towards a center of the slot.

19. The method according to claim 17, further comprising fastening the bone plate to at least three vertebrae along the anterior cervical spine.

20. The bone plate according to claim 10, wherein the bone plate is a monolithic structure.

* * * * *